United States Patent [19]
Springer, Jr.

[11] Patent Number: 5,527,357
[45] Date of Patent: Jun. 18, 1996

[54] APPARATUS FOR TONING FACIAL TISSUE

[76] Inventor: George E. Springer, Jr., 1827 Oak Lake Dr., Clearwater, Fla. 34624

[21] Appl. No.: 265,605

[22] Filed: Jun. 24, 1994

Related U.S. Application Data

[63] Continuation-in-part of Ser. No. 111,341, Aug. 24, 1994, abandoned.

[51] Int. Cl.⁶ ..................................................... A61N 1/26
[52] U.S. Cl. .............................................. 607/140; 607/74
[58] Field of Search ...................... 128/897–898; 607/48, 63, 139, 140, 152, 74–75, 156

[56] References Cited

U.S. PATENT DOCUMENTS

| | | | |
|---|---|---|---|
| 1,692,669 | 11/1928 | Last | 607/140 |
| 2,191,080 | 2/1940 | Lewis | 607/139 |
| 2,433,233 | 12/1947 | Meminger | 607/139 |
| 3,279,468 | 10/1966 | Le Vine | 607/139 |
| 3,971,387 | 7/1976 | Mantell | 607/139 |

Primary Examiner—William E. Kamm
Attorney, Agent, or Firm—Joseph C. Mason, Jr.; Louise A. Foutch; Ronald E. Smith

[57] ABSTRACT

A galvanic current is applied to acupuncture points of a human face by electrodes that are mounted in a predetermined array on a mask-like device that overlies the face. Each electrode is movable along its longitudinal axis so that its leading end is positionable into abutting relation to the face of the wearer of the mask. A low voltage is applied to each electrode and facial tissue is stimulated by a galvanic current that flows between the electrode and a remote ground. An electronic circuit controls activation of each electrode in accordance with a predetermined pattern to provide an optimal, systematic treatment, but the circuit may be overridden in favor of a manual activation of the electrodes so that the treatment may be provided in accordance with any pattern. A rubber sheath overlies the leading end of each electrode and has an enlarged, disc-shaped leading end to ensure treatment of all areas of the face that require stimulation.

5 Claims, 5 Drawing Sheets

U.S. Patent     Jun. 18, 1996     Sheet 1 of 5     5,527,357
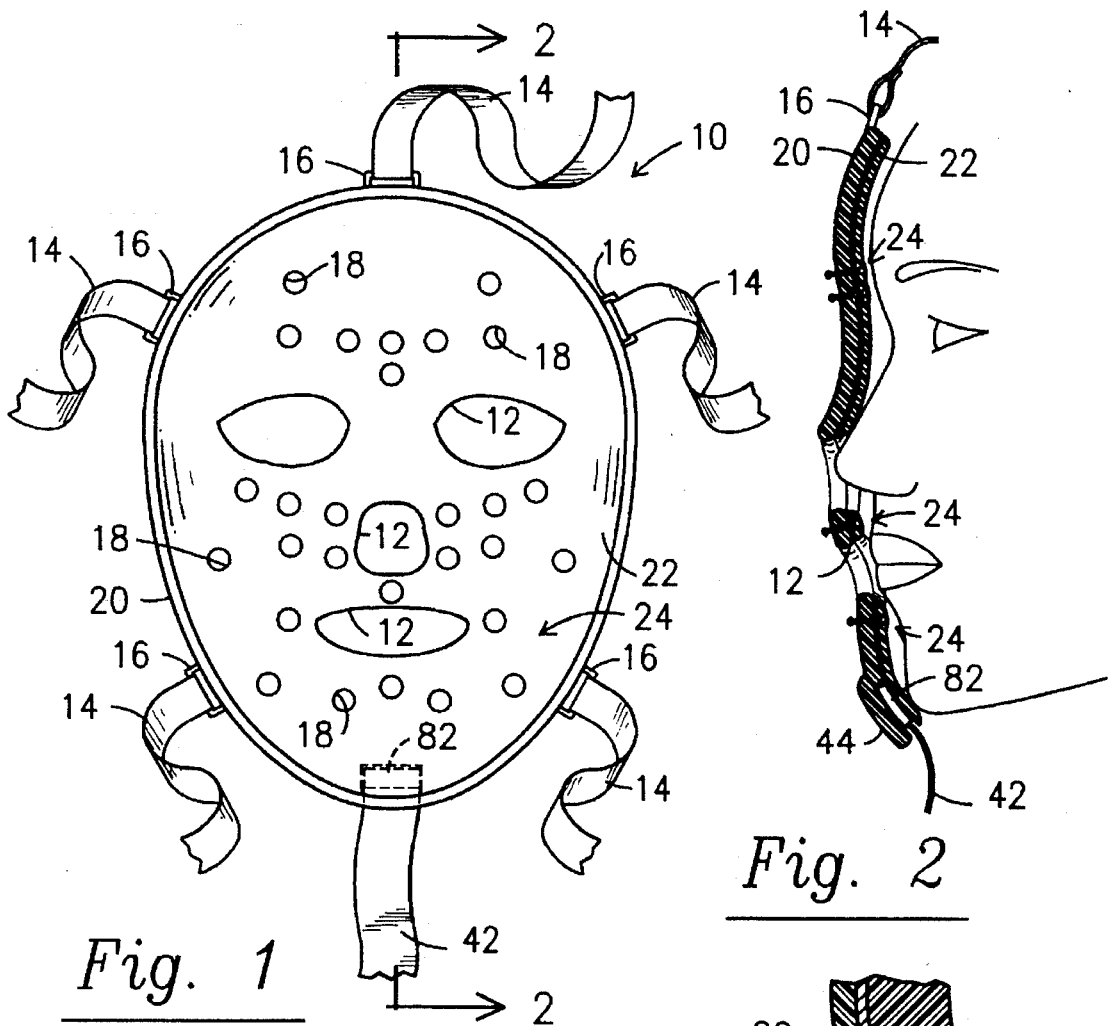
Fig. 1
Fig. 2
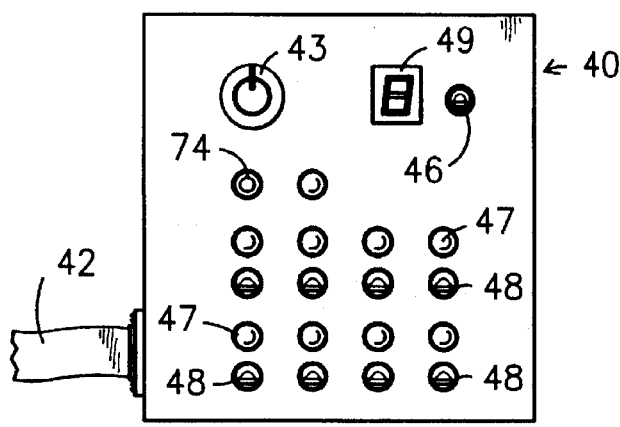
Fig. 4
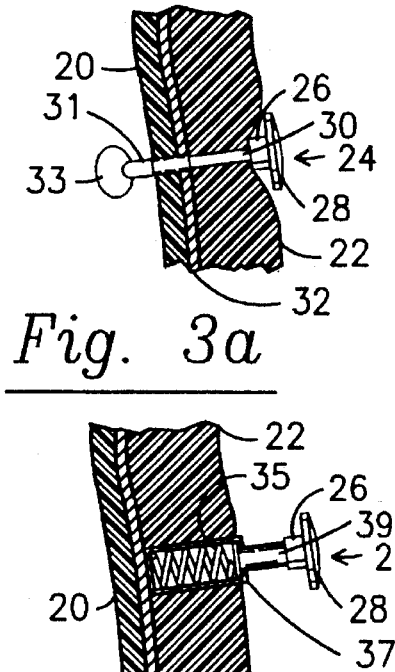
Fig. 3a
Fig. 3b

APPARATUS FOR TONING FACIAL TISSUE

This is a continuation-in-part of application Ser. No. 08/111,341 filed on Aug. 24, 1994 now abandoned.

BACKGROUND OF THE INVENTION

1. Field of the Invention

This invention relates, generally, to means and methods for toning and lifting facial tissue.

2. Description of the Prior Art

The aging process includes loss of tone of facial tissue; such loss of tone manifests itself in wrinkles, sagging skin, and the like. Chinese acupuncture has some utility as an effective treatment for the condition, but many people either fear acupuncture, can't afford it, or live in areas of the country where it is not available. Moreover, if the acupuncturist does not treat the user in a comprehensive, systematic fashion, the treatment may be unsatisfactory.

In an effort to avoid the use of needles, some inventors have developed treatments that rely upon non-penetrating electrodes to establish galvanic currents in the facial muscle being treated. One example of such a treatment appears in U.S. Pat. No. 4,957,480 to Morenings; it involves electrical stimulation of muscle in such a way as to cause the muscle to contract, in the hope that stronger muscles beneath the skin will reduce sagging of the skin. A pair of hand-held electrodes are positioned on opposite sides of the muscle to be contracted so that current flow between the electrodes also flows through the muscle. This requires the individual performing the treatment to painstakingly move the electrodes from muscle to muscle and thus is somewhat time-consuming. Moreover, if the treatment provider is unskilled or does not know the positions of all the muscles, the treatment may be ineffective.

Other treatments eschew the use of electrodes and rely instead on the principles of isometric exercise. U.S. Pat. No. 4,892,092 to Klein, for example, shows a mask worn by an individual desiring to improve facial muscle tone. When the mask is worn, a plurality of pressure applicators overlie preselected parts of the face; specifically, each pair of applicators overlies opposite ends of preselected muscles. Means are provided to cause the pressure applicators to displace in a direction towards the face so that the muscles are held against movement by the applicators at opposite ends thereof. The person wearing the mask then attempts to contract the muscles and the benefits of isometric exercise are thereby attained. Considerable amounts of pressure may be required at opposite ends of the stronger muscles, and the treatment will work only if the person receiving the treatment performs the muscle contractions properly.

Still another device for beauty treatment is shown in U.S. Pat. No. 4,117,837 to Remiro. The device is an elastomeric mask that conforms to the shape of the wearer's face. The benefits derive from the elastic action of the mask against the facial skin; no particular points are treated differently than all other points.

U.S. Pat. No. 3,279,468 to Le Vine includes a mask having a plurality of paired electrodes disposed throughout. The electrodes of each pair are closely spaced to one another and one member of the pair serves as ground so that current flows only between the paired electrodes. The current activates the motor fibers of a particular muscle group. The mask has a pegboard-like appearance so that the electrodes may be moved further apart or closer together. Thus, the therapist must have an advanced knowledge of muscle structure in order to properly position each electrode pair. Moreover, the pegboard-like structure of the mask limits the therapist to horizontal and vertical relocations of individual electrodes.

A moist pad overlies the user's face as a part of the treatment procedure described in U.S. Pat. 3,971,387 to Mantell, and is held in place by a mask strapped in overlying relation thereto. Plural, nonadjustable buttons are riveted onto the mask and their placement is not in accord with motor points of the facial muscles, acupuncture points, or any other anatomically significant points. Moreover, all buttons are electrically stimulated at the same time.

Thus, there is a need for a facial tissue toning device and method that does not require the person performing the treatment to move a pair of electrodes from position to position. Moreover, the ideal device would not subject its user's face to high pressures and would not require the individual receiving the treatment to perform isometric exercises. The ideal device would also provide treatment for specific, critical points on the face and finding such points would not be left to the skill or knowledge of the treatment provider.

However, when the prior art is considered as a whole, it neither teaches nor suggests to those of ordinary skill in this art how the ideal device could be provided.

SUMMARY OF THE INVENTION

The longstanding but heretofore unfulfilled need for an apparatus and method for improving the tone of facial muscles and tissue is now fulfilled by a highly novel structure that performs the toning function in the absence of acupuncture needles, in the absence of hand-held electrodes, in the absence of high pressures on the user's skin and in the absence of any need for the user to perform isometric exercises. Significantly, the novel device always applies the treatment to the points of the face where treatment is needed.

In both prototype and commercial embodiment form, the novel device is provided in the form of a mask that is worn over the face of the user. In the prototype form, the mask includes a relatively soft, thick inner lining that lightly and comfortably overlies the face of a user when the device is worn, a somewhat rigid outer lining that provides the required structural integrity, a thin sheet, having electrically conductive paths imprinted thereon, disposed in sandwiched relation between the outer and inner linings, and a plurality of electrodes that are mounted in a predetermined array. Each electrode is received within its associated throughbore formed in the inner lining and is movable within its bore along its longitudinal axis so that it may conform to differing facial sizes and shapes. The trailing end of each electrode is in electrical contact with its associated electrically conductive path, and the leading end of each electrode contacts the user's face.

In one commercial embodiment, the thin sheet having the paths imprinted thereon is eliminated. Instead, the electrically conductive paths are electroplated onto a catalytic resin that is injection molded into predefined areas of the outer lining that are in turn created by an injection molding process. Each electrode includes a mounting post that is formed during the injection molding process. The face-contacting part of each electrode has a trailing end that screw-threadedly engages its associated mounting post; thus, its longitudinal position is adjusted by rotation.

In another, more developed commercial embodiment, the device includes an inner mask, an outer mask, a thick, resilient foam pad disposed in sandwiched relation between said inner and outer masks, a flexible sheet having an electronic circuit imprinted thereon, said flexible sheet being disposed in sandwiched relation between the inner mask and the foam pad, and a plurality of movably mounted electrodes having a first end disposed in electrical communication with the electronic circuit and a second end disposed in contacting relation to the user's face. When the device is worn, the electrodes contact the user's face and the firmness of the face drives the electrodes into the foam pad, i.e., the foam pad serves as a biasing means that biases the electrodes toward the user's face. The electrical circuit is flexible so that it gives with the electrode.

In all embodiments, the position of each electrode with respect to the differing parts of the mask is specifically predetermined so that each electrode touches a critical part of the user's face when the electrode is extended into abutting contact with the face. Each electrode is in electrical communication with electronic circuitry that includes timing means for activating and deactivating each electrode in accordance with a predetermined pattern to provide an optimal treatment, but the user may override the circuitry and perform the treatment in any pattern desired.

Significantly, the ground for the device is spaced away from the electrodes so that current flows a relatively long distance, i.e., not just between a pair of closely spaced apart electrodes as in the Le Vine disclosure mentioned above. Specifically, the ground points are located along the jaw line of the device; the current thus has a broader effect on circulation and facial tissue. Moreover, the locations of the electrodes correspond to known acupuncture points; thus, the application of an electrical potential to a particular electrode may have a toning effect on a part of the face spatially separate from the activated electrode. Since the acupuncture points are located in substantially the same place for everybody, no trained therapist knowledgeable in facial anatomy is required to operate the device as in most of the earlier devices in this field.

Thus, it should be clear that the primary object of this invention is to provide an apparatus that tones facial muscle and tissue.

A more specific object is to provide such an apparatus that is comfortable to wear and which does not subject its user to uncomfortable pressures or needles.

Still another object is to provide an apparatus that positions each of the muscle-stimulating electrodes in an effective position on the face when the mask is worn so that the user need not be knowledgeable concerning the optimal position of each electrode.

Another object is to provide electronic means for sequencing the activation of each electrode so that the treatment is performed quickly but effectively.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a front elevational view of the novel mask;

FIG. 2 is a sectional view thereof taken along line 2—2 in FIG. 1;

FIG. 3A is a detailed side elevational view of a first embodiment of a movably mounted electrode;

FIG. 3B is a detailed side elevational view of a second embodiment of a movably mounted electrode;

FIG. 4 is a front elevational view of an illustrative control panel for use with this invention;

DETAILED DESCRIPTION OF THE PREFERRED EMBODIMENT

Figure 5:
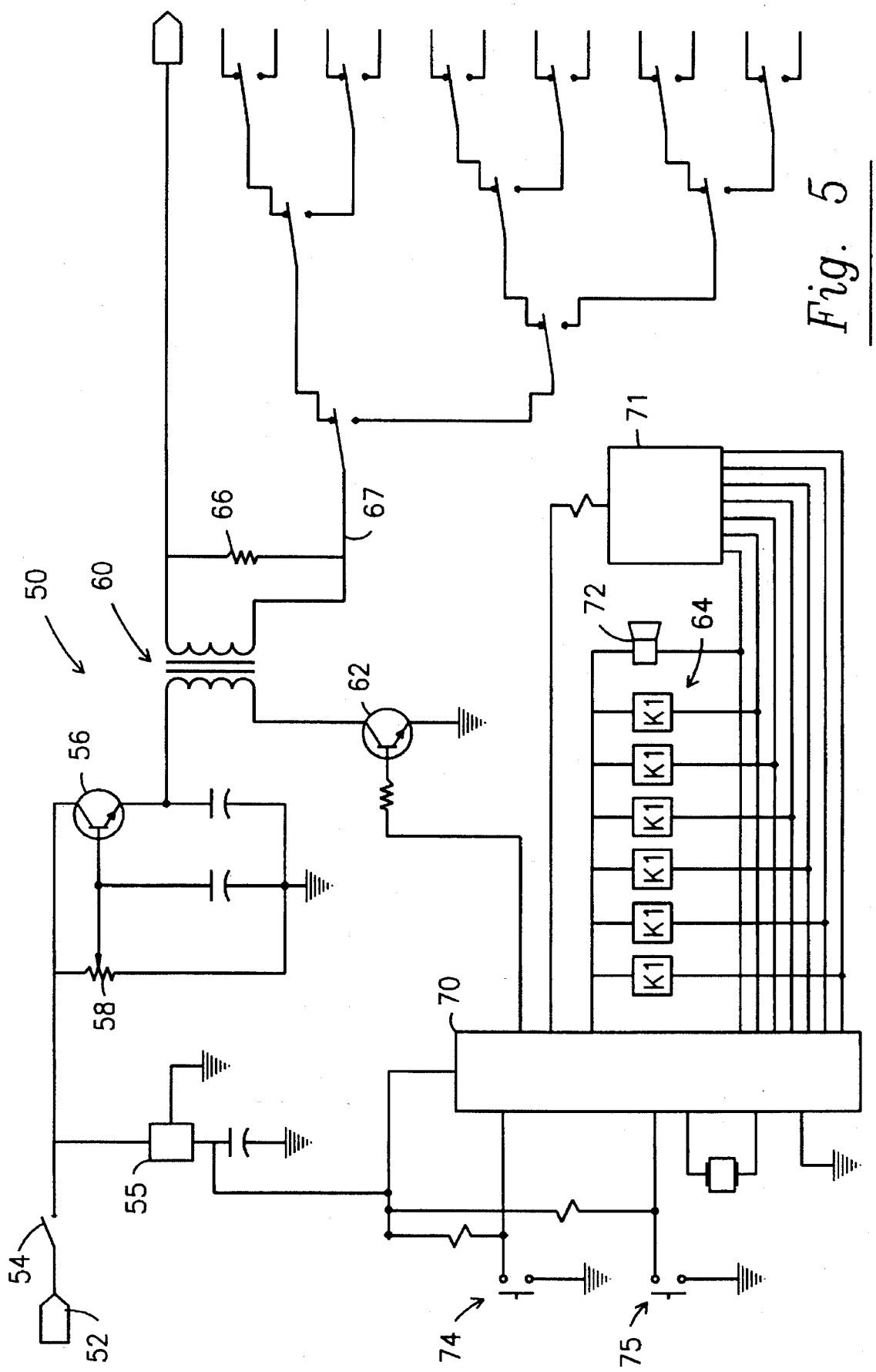
FIG. 5 is an illustrative electrical schematic diagram of the control circuitry.

Referring now to FIG. 1, it will there be seen that the novel mask, in prototype form, is denoted as a whole by the reference numeral 10. The large openings formed therein are collectively denoted 12 and accommodate the user's eyes, nose and mouth. Straps, collectively denoted 14, are circumferentially spaced apart with respect to one another about the periphery of mask 10 and are employed to maintain the mask in a fixed position relative to the user's face during the treatment. The mounting members to which the straps are secured are collectively denoted 16.

Reference numeral 18 denotes the respective electrodes; they are shown in phantom lines because the throughbores formed in the inner lining do not extend through the outer lining.

The construction of mask 10 in prototype form is set forth in additional detail in FIG. 2. There it will be seen that the thin, hard plastic exterior lining of the mask is denoted 20 and that the thick, soft inner lining thereof is denoted 22. A flexible sheet 32 is sandwiched therebetween; said sheet is the substrate upon which is imprinted the electrical conductors that distribute power to the individual electrodes, as will be more fully set forth hereinafter. In a commercial embodiment, sheet 32 is not employed; instead, a substrate 32 is applied to lining 20 so as to be integrally formed therewith, as more fully set forth hereinafter.

The electrodes of this embodiment are collectively denoted 24; each electrode includes a cylindrical base 26 and a disc-shaped head 28 that contacts the user's face when the invention is in use. As will become more clear as this description proceeds, base 26 and head 28 form a sheath, preferably of rubber construction, that fits onto the metallic part of the electrode. An electrically conductive gel is applied to the rubber sheath to make it electrically conductive. As shown in FIG. 2, when the mask is in use, only head 28 of each electrode contacts the user's face.

Head 28 is enlarged so that it covers a large surface area of the user's face when the invention is in use, thereby ensuring that all areas of the face that require treatment will be treated, i.e., the relatively large size of head 28 provides a fudge-factor so that the mask may be used with people having varying facial sizes and shapes. Although masks of differing sizes and shapes are within the scope of this invention, it should be noted that the facial structure of most people, i.e., the distance between the eyes and the like, varies only by a millimeter or two.

In a first embodiment of the mounting means for each electrode, depicted in FIG. 3A, an externally threaded metallic rod 30 engages the interior sidewall of cylindrical base 26, and an internally threaded tube 31, having knob 33 to facilitate its turning, screw-threadedly engages said rod 30. Tube 31 is rotationally mounted within its associated throughbore, but is not longitudinally displaceable. Thus, rotation of said tube in a first direction causes advancement of rod 30 and hence electrode 24 toward the user's face, and counterrotation causes retraction of said rod and electrode.

In the exemplary embodiment of FIG. 3B, a metallic, unthreaded casing 37 houses bias means 35 which urges head 28 toward the user's face. A post 30 is slideably received within said casing 37 and the leading end of said post is press fit within cylindrical part 26 of electrode 24.

Figure 3C:
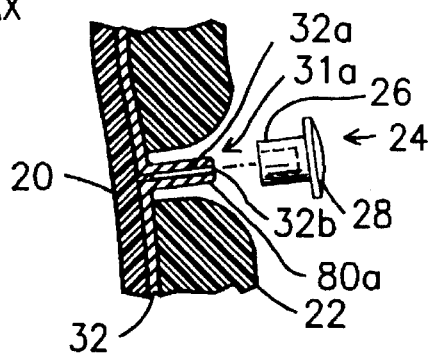
FIG. 3C is a detailed side elevational view of a third embodiment of a movably mounted electrode.

In the structure depicted in FIG. 3C, each mounting post 32a is formed of resin and is formed integrally with the resin that forms substrate 32 during the molding process disclosed below. Most of the external surface area of each post 32a is covered with a thin layer of copper 80a during the electroplating process described below, but a pair of diametrically opposed strips 20b, only one of which may be seen in the Fig., are left unplated as shown. Internally threaded tubular member 26, of metallic construction, is secured to electrode head 24 in the manner depicted. Its internal threads engage the exposed resin strips 32b; said engagement serves to lock the tubular member in place so that head 24 remains in whatever position of adjustment is selected for it. External threads may also be formed in the copper-plated part of each post 32b to further enhance the engagement between each post and tubular member 26.

Figure 3D:
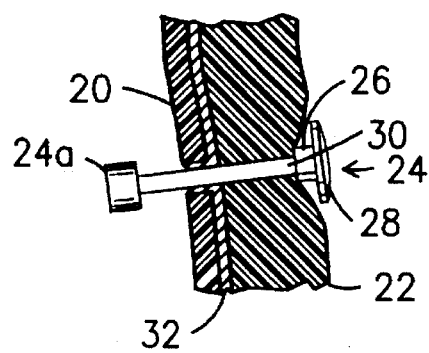
FIG. 3D is a detailed side elevational view of a fourth embodiment of a movably mounted electrode.

FIG. 3D provides a movably mounted electrode that is easy to use. As shown, it impales the novel mask, i.e., it is slidingly but tightly received within a throughbore formed in the mask structure. A handle 24A is formed in the trailing end of post 30; thus, the user merely needs to push on said handle 24a until head 28 of electrode 24 is seated comfortably against the user's face. The handle 24 is just as easily pulled away from the face if the pressure becomes uncomfortable. The interior of the throughbore and the exterior or post 30 are copper coated to provide the required electrical communication.

Figure 3E:
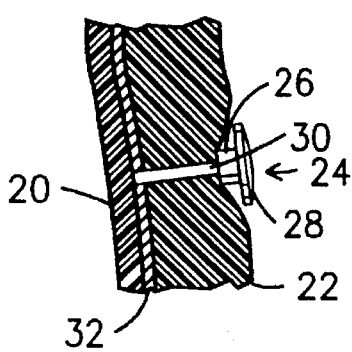
FIG. 3E is a detailed side elevational view of an immovably mounted electrode.

FIG. 3E shows a structure that does not provide means for adjusting the axial displacement of the individual electrodes. It includes a rod 30 that is immovably press fit within cylindrical base 26; note that the trailing end of rod 30 is in electrical contact with conductive substrate 32.

An electrical potential of nine volts is applied to the trailing end of each post 30, screw 31, or casing 37, resulting in a current that flows from the activated electrode to ground and thus stimulates the user's facial tissue. The current is applied through a plurality of flat, preferably copper conductors 80 (FIG. 8) imprinted upon sheet 32 that is sandwiched between outer liner 20 and inner liner 22 in the prototype form of the invention as mentioned above. Accordingly, the voltage may be applied to each electrode on a selective basis in any pattern.

Control box 40, shown in FIG. 4, contains a power supply 52 and the electrical circuitry that selectively distributes the voltage to the conductors 80 and hence to electrodes 24; it also includes means for overriding the circuitry so that the user may apply the voltage in any pattern and for any time duration desired by the user.

Figure 7:
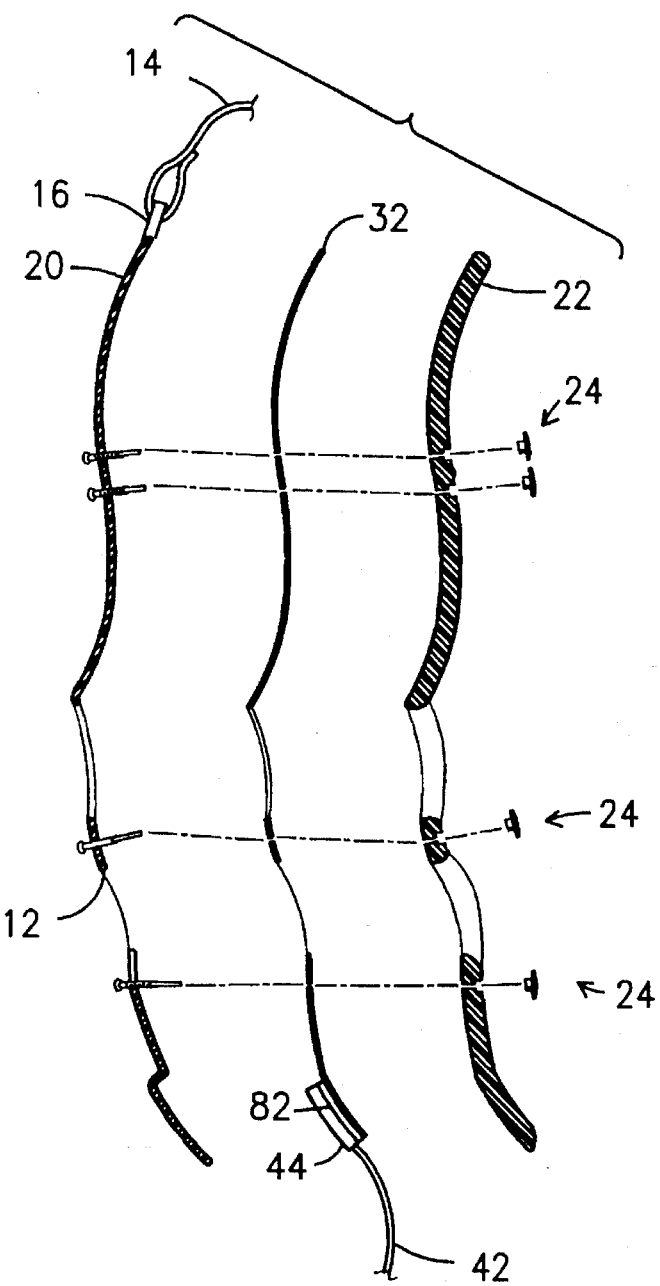
FIG. 7 is an exploded side elevational view of the outer liner, flexible sheet, and inner liner that collectively form the novel mask in prototype form.

Flat cable 42 provides electrical communication between the control box and the mask; coupler 44 at the distal end of cable 42, as shown at the respective bottoms of FIGS. 2 and 7, is a conventional computer-type connector and is releasably plugged into socket 82 (FIGS. 1, 7 and 8) at the bottom of the mask.

Switch actuator 46 is a power on-off switch. A plurality of switch actuators, collectively denoted 48, are manual switch actuators for activating the electrodes in a pattern determined by a user when the predetermined pattern of electrode activation is not desired. For example, a user may have one particular wrinkle that requires extra treatment, or portions of the face that require no treatment. In such situations, the user may eschew the predetermined patterns of the machine and manually activate only those electrodes of most importance to the user by throwing the switch actuators of the user's choice. An LED lamp 47 associated with each manual switch actuator 46 indicates which electrode is in use; such lamps operate when the machine is in its automatic mode or in its manual mode. Dial 47 is an intensity control means; it enables the user to adjust the amount of voltage applied to the electrodes and is of PNPN construction. Display means 49 indicates the electrode number to which current is flowing in real time.

Turning now to FIG. 5, it will there be seen that the novel circuitry is denoted 50 as a whole. Power is supplied by nine volt battery 52; regulated power is supplied by low power three terminal regulator 55. Transistor 56 is a variable voltage regulator controlled by resistor 58; said resistor 58 performs an intensity selector function which could, alternatively, be performed by a suitable switch means. The output of transistor 56 is applied to transformer 60 which is under the control of microprocessor 70 through transistor 62. Transformer 60 isolates and couples the signal to a bank of relays, collectively denoted 64, that perform the function of selecting which copper path 90 and hence which electrodes will be activated.

In a preferred embodiment, transformer 60 is a Mouser type MC001, relays 64 are Aromat TF series, and microprocessor 70 is a Microchip 16C54.

Figure 6:
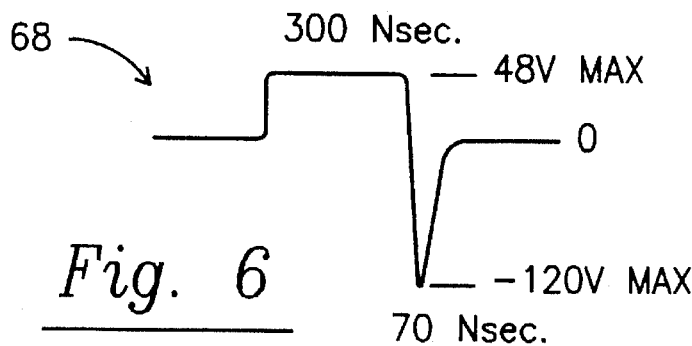
FIG. 6 depicts a waveform of a signal at a preselected part of the circuitry.

Current limiting resistor 66 limits the signal power applied to the electrodes. The waveform at point 67 of the circuit under no-load conditions is a square wave with a negative spike, as shown in FIG. 6 as at 68. The pulse width is three hundred microseconds, and the pulse rate is 7.8 Hz. The amplitude peak value is 56 mA at 250 ohm load, and the adjustable voltage intensity is 48–120 volts at no load and 2.5–14 volts at 250 ohm load.

When start button 75 is pushed, microprocessor 70 times the stimulation pulses as 7.8 Hz and routes them, one at a time, i.e., in a predetermined sequence, to the appropriate electrodes, via relays 64. As the electrodes are activated, LED lamp 47 (FIG. 4) associated with each electrode is lit so that the user knows which electrodes are being activated. Chime 72 sounds when all electrodes have been activated, indicating that the treatment is over and that the mask may be removed. Microprocessor 70 then shuts itself off to conserve battery life. To repeat the treatment, the unit must be turned off and back on again.

Test button 74, upon initial activation after power is supplied to the unit, causes voltage to be supplied to electrode number 1. Upon subsequent activation, it causes voltage to be supplied to electrode number 2, and so on. Thus, test button 74 may be used to test each electrode and to override the predetermined sequence of microprocessor 70.

Figure 8:
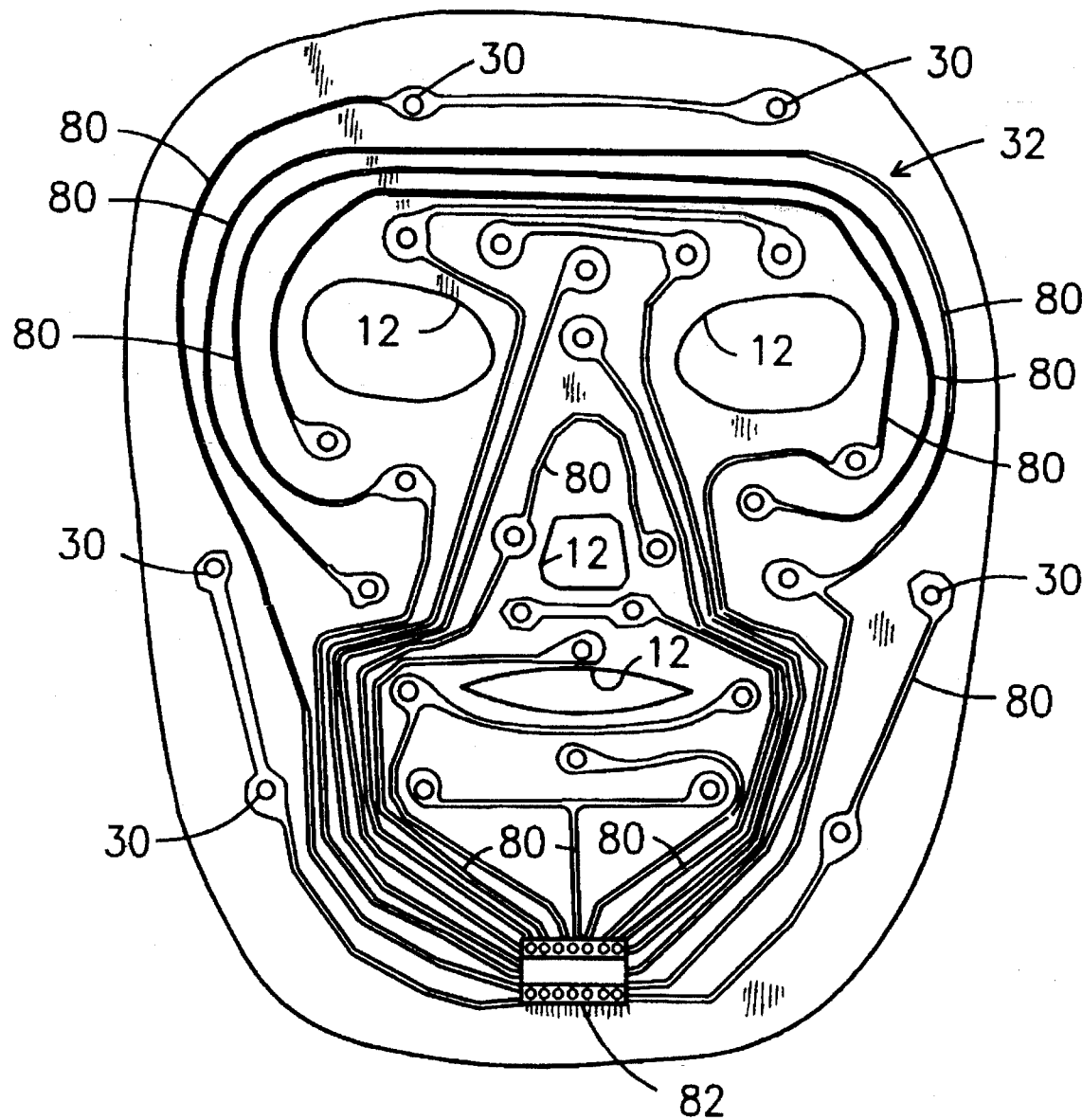
FIG. 8 is a rear elevational view of the inner liner of the mask, showing an early commercial embodiment having the electrically conductive paths electroplated thereon.

The exploded view of FIG. 7 shows how the prototype of the inventive device is assembled. FIG. 8 is a frontal view of flexible sheet 32, showing copper conductors 80 imprinted thereon. Note that, in this particular embodiment, each conductor is connected to more than one electrode; however, a mask construction having a separate conductor for each electrode is also within the scope of this invention. Socket 82 at the bottom of FIG. 8 is the receptacle for plug 44, as mentioned above; its pins are individually in electrical communication with the various conductors 80. Thus, it should be understood that the pattern of electrode activation is controlled by distributing power to said pins in the desired sequence.

One commercial embodiment of the invention does not include flexible sheet 32 as an independent structural part thereof, as mentioned above. Nonetheless, its physical appearance is the same as the structure shown in FIG. 8 and FIG. 8 should therefore be understood as depicting said commercial embodiment. In said commercial embodiment, the copper conductors 80 are applied to the inner surface of outer lining 20 by injection molding and electroplating processes. More particularly, a noncatalytic resin (inert to electroplating current) is injected into a first mold cavity to form outer lining 20. A plurality of predefined, recessed areas, which become the conductive pathways for distributing current to the electrodes, are formed in the inner surface of the outer lining during this initial step of the process. Each mounting post 31a is also formed during this initial step. The outer lining with said predefined areas and mounting posts formed therein is hereinafter referred to as the base. The base is next inserted into a second mold cavity and a suitable plateable catalytic resin is injected into said predefined, recessed areas and is also applied to each mounting post to form a substrate onto which copper is electroplated. Prior to the electroplating process, however, the substrate is chemically treated to enhance said electroplating process. After a thin film of copper has been deposited onto the chemically treated catalytic resin substrate by the electroplating process, (leaving diametrically opposed strips 32b unplated), the assembly is placed into a third mold cavity where the soft inner lining 22 is formed by injection molding; significantly, said soft inner lining covers the copper conductive pathways to conceal them from view and provides a soft surface for the comfort of the wearer of the novel mask, as mentioned earlier.

The above-described injection molding technique is performed by Mitsui-Pathtek corporation of Rochester, N.Y.; additional details of the process may be obtained from that company, but those of ordinary skill in the injection molding art can make and use the novel mask from the above description without contacting said company and without undue experimentation.

The injection molding process just described also enables the molding of socket 82 as an integral part of the mask at the time the molding process is performed.

The face-contacting disc-shaped parts 24 are then attached to their associated metallic fasteners 26 by an extruding process. In a commercial embodiment of the facial electrodes, depicted in FIG. 3C, disc-shaped parts 24 are formed of electrically conductive silicone extruded to said internally threaded metal fastener 26. In view of the screw-threaded relationship of the internal threads of fastener 26 and the exposed plastic strips 32b of post 31a, rotation of part 24 in a first direction advances it towards the wearer's face, and rotation in a second direction moves it away from the wearer's face. Thus, it should be understood that the injection molding procedure produces the mounting posts as an integral part of the mask; therefore, it is a simple, one step procedure to complete the mask assembly by screwing each part 24 onto its associated post. It is an equally simple matter for the consumer to adjust each part 24 to the position suitable for that person's facial shape and size.

Figure 10:
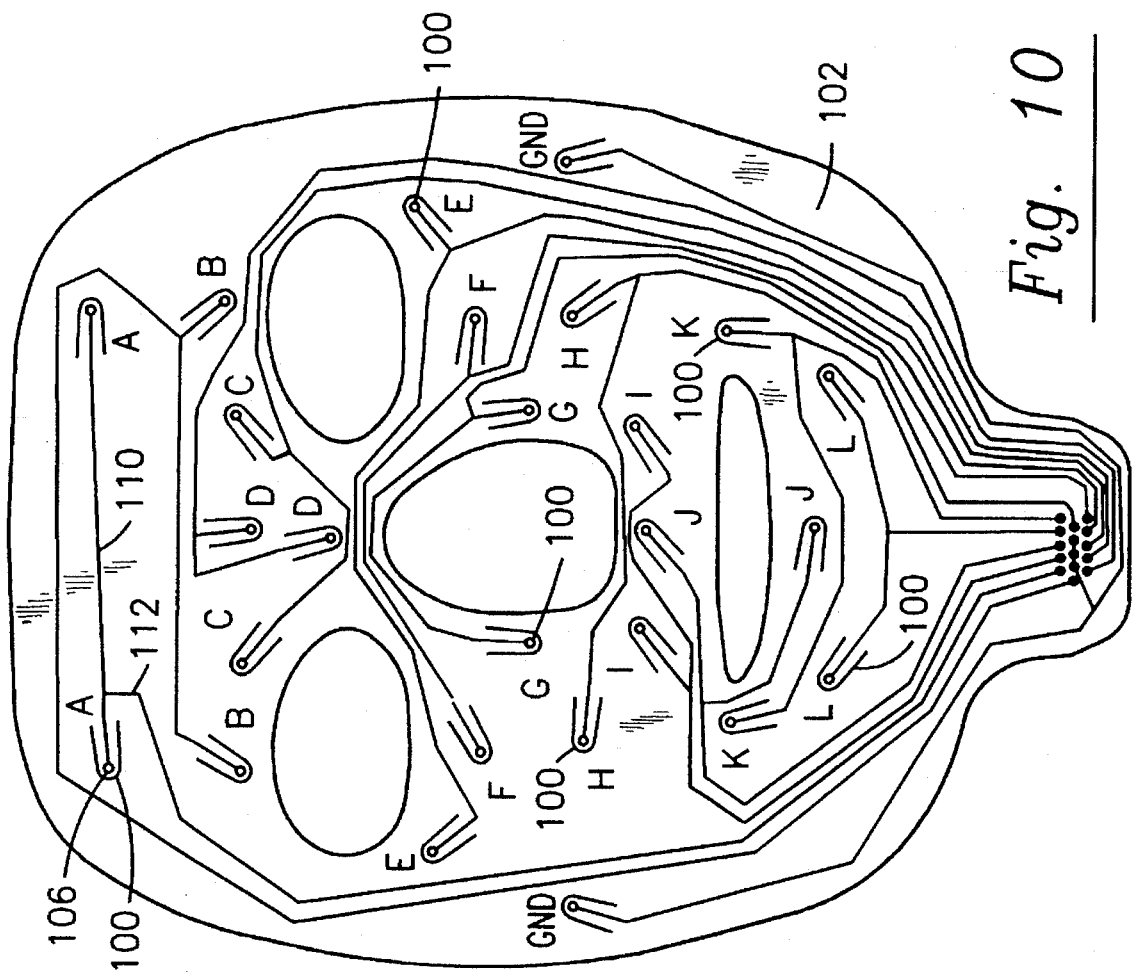
FIG. 10 is a rear elevational view of the flexible sheet having the novel electronic circuitry imprinted thereon.
Figure 9:
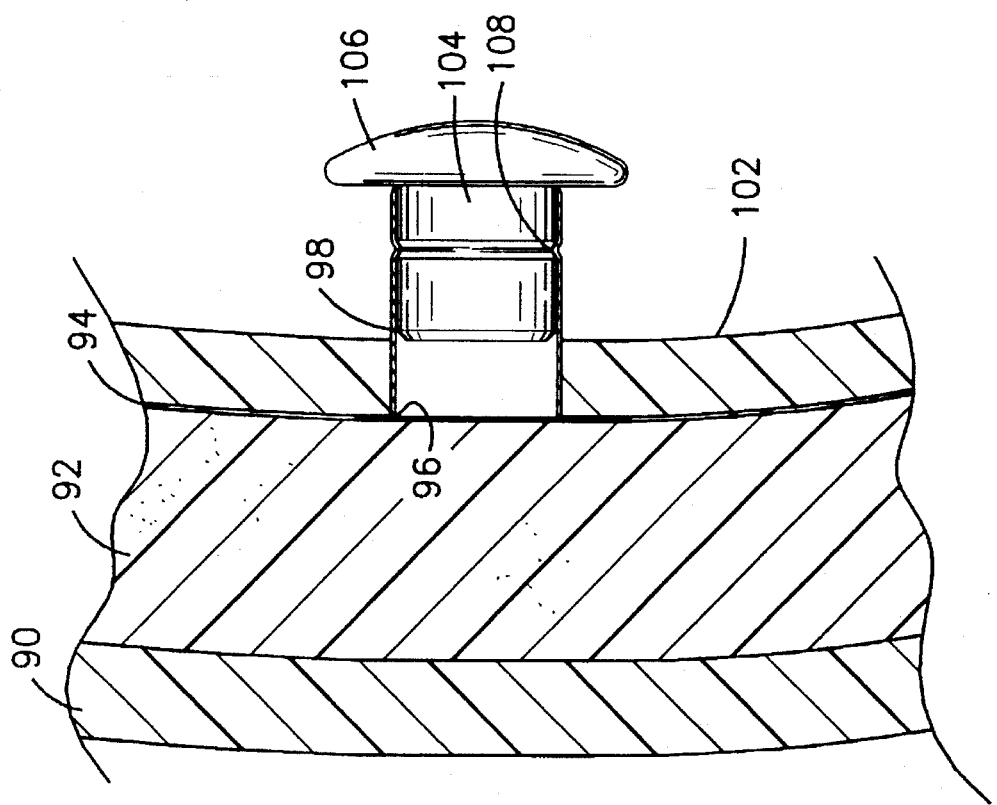
FIG. 9 is a sectional view of a more developed commercial embodiment of the novel structure.

A more developed commercial embodiment of this invention is depicted in FIGS. 9 and 10. As disclosed in FIG. 9, an improved outer mask lining 90 is made of a flexible yet rigid plastic having brow and cheek contours formed thereinto to allow full extension of the facial contact electrodes into such areas when exterior pressure is applied.

A relatively thick layer of soft, resilient, cushioned foam 92 underlies outer lining 90 and provides biasing means for the individual electrodes as will become clear as this disclosure proceeds.

Flexible circuit board 94 underlies foam 92; it includes conductive paths as shown to provide electrical communication between the power supply and all electrodes. A throughbore 96 is formed in circuit board 94 at each electrode location, and a cylindrical brass eyelet 98 is welded or otherwise secured thereto. As best understood in connection with FIG. 10, a U-shaped slit 100 is cut into board 94 at each eyelet 98; accordingly, as pressure is applied to an eyelet in a direction normal to the plane of the paper in FIG. 10, board 94 flexes in the region of the eyelet. The direction of flex in FIG. 10 is into the paper, i.e., toward foam cushion 92.

The inner lining of the mask is denoted 102 in FIG. 9; it is made of the same plastic as outer lining 90, but a throughbore is formed therein at each electrode position whereas outer lining 90 is imperforate.

A conductive rubber plug 104 having face-contacting head 106 is inserted into eyelet 98 and is retained therewithin for simultaneous and conjoint displacement therewith by radially inwardly extending annular detent 108 formed in said eyelet, said detent being received within a complementally formed annular valley formed in plug 104 as depicted. A conductive gel may be applied to head 106 to enhance the electrical contact between said head 106 and the user's face. This type of connection enables facile replacement of the plugs so that beauty salons and the like may change said plugs as frequently as desired. Note that head 106 of plug 104 remains in electrical communication with its associated electrical conductive path at all times and said contact is neither established nor broken as a result of the displacement of plug 104 along its longitudinal axis of symmetry when the mask is put on and taken off.

Note in FIG. 10 that the points denoted "A" and "A'" are interconnected by conductor 110 and that both of them are connected to the microprocessor by conductor 112. Thus, both points are brought to the nine volt potential at the same time, i.e., in this embodiment, point "A" cannot be activated without also activating "A'" and vice versa. This prevents nonsymmetrical treatment of the facial muscles. Note further that current flows between point "A" and ground point "Gnd" and between "A'" and "Gnd'"; again, this insures symmetrical treatment. Note further the long distance between said points "A" and "A'" and their respective grounds; current flows this entire distance, thereby providing therapeutic effect along said entire distance. More importantly, points "A" and "A'" are acupuncture points, as are all of the other depicted points.

Note that all points "B," "B'," "C," "C', " etc. exhibit bilateral symmetry with their counterpart, and are interconnected by a conductor so that each set of like-named points is always brought to the treatment potential at the same time and that current flow is always from each point to the closest ground. Thus, each established current exhibits bilateral symmetry with a counterpart current so that both sides of the user's face are treated equally.

This invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A device for toning facial muscles, comprising:

a flexible electrical circuit board;

an inner liner adapted to be disposed in closely spaced relation to a human face when the device is worn;

a plurality of throughbores formed in said inner liner, each of said throughbores being in substantial alignment with an acupuncture point on said human face when said device is worn;

an electrode extending through each of said throughbores;

each electrode having a leading end adapted to contact a user's face and each electrode having a trailing end disposed in abutting, electrically conducting relation to said flexible electrical circuit board when said device is worn;

a power source for selectively supplying a predetermined voltage to each electrode;

said flexible electrical circuit board including an electrically conductive path interconnecting said power source and each electrode;

means enabling users of differing facial structures to use said device;

said means including a resilient cushion means for biasing each electrode toward said user's face;

said flexible electrical circuit board being disposed in sandwiched relation between said inner liner and said resilient cushion means;

a "U"-shaped cut formed in said flexible electrical circuit board that partially surrounds each electrode to permit flexing of said flexible electrical circuit board when an electrode is displaced by its leading end abutting said user's face when the device is worn and to limit the flexing of said flexible electrical circuit board to an area contiguous to a displaced electrode, said contiguous area being bounded by said "U"-shaped cut;

an outer liner disposed in abutting relation to said resilient cushion means;

said resilient cushion means and said flexible electrical circuit board being disposed in sandwiched relation to said outer liner and said inner liner;

a pair of electrical grounds positioned in a jaw line area of said flexible electrical circuit board on opposite sides of said flexible electrical circuit board in laterally spaced apart relation to one another to promote symmetrical toning of facial muscles, said pair of electrical grounds being remote from each of said electrodes;

whereby activation of said power source causes current to flow to said pair of electrical grounds from a predetermined pair of electrodes so that both sides of a user's face are treated symmetrically, 2. The device of claim 1, further comprising distributing means for selectively distributing voltage to each of said electrodes in accordance with a predetermined sequence.

3. The device of claim 2, wherein said distributing means is a microprocessor.

4. The device of claim 1, wherein each electrode includes a cylindrical eyelet secured to said flexible electrical circuit and a conductive rubber plug removably mounted within said cylindrical eyelet.

5. The device of claim 1, further comprising a plurality of large openings formed in said inner liner, said outer liner, and said flexible electrical circuit board for accommodating the eyes, nose, and mouth of said user's face.

* * * * *